(12) United States Patent
Chinnadurai et al.

(10) Patent No.: US 10,729,719 B1
(45) Date of Patent: Aug. 4, 2020

(54) FRUIT-DERIVED CORE-SHELL NANOSPHERES

(71) Applicant: KING SAUD UNIVERSITY, Riyadh (SA)

(72) Inventors: Veeramani Chinnadurai, Riyadh (SA); Khalid S. Al-Numair, Riyadh (SA); Mohammed A. Alsaif, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/656,532

(22) Filed: Oct. 17, 2019

(51) Int. Cl.
| | |
|---|---|
| *A61K 33/38* | (2006.01) |
| *A61K 9/16* | (2006.01) |
| *A61K 36/185* | (2006.01) |
| *A61P 35/00* | (2006.01) |

(52) U.S. Cl.
CPC ............. *A61K 33/38* (2013.01); *A61K 9/167* (2013.01); *A61K 9/1617* (2013.01); *A61K 36/185* (2013.01); *A61P 35/00* (2018.01)

(58) Field of Classification Search
None
See application file for complete search history.

(56) References Cited

FOREIGN PATENT DOCUMENTS

| | | |
|---|---|---|
| CN | 106432154 A | 2/2017 |
| CN | 106954802 A | 7/2017 |
| CN | 107779342 A | 3/2018 |

OTHER PUBLICATIONS

Sathya Prabhu, Shanmugam Vinodhini, Chakravarthy Elanchezhiyan, and Devi Rajeswari. Evaluation of antidiabetic activity of biologically synthesized silver nanoparticles using Pouteria sapota in streptozotocin-induced diabetic rats. Journal of Diabetes 10 (2018), 28-42. (Year: 2018).*

Google patent search: silver nanoparticles fruit extract core-shell. Jan. 30, 2020 (Year: 2020).*
Google patent search: silver nanoparticles fruit extract. Jan. 30, 2020 (Year: 2020).*
Google patent search: silver nanoparticles plant extract king saud university. Jan. 30, 2020 (Year: 2020).*
Google search: pouteria sapota and pouteria caimito. Jan. 30, 2020 (Year: 2020).*
Cíntia A. M. Silva, Luiz A. Simeoni, Dâmaris Silveira. Genus *Pouteria*: Chemistry and biological activity. Brazilian Journal of Pharmacognosy 19(2A): 501-509, Apr./Jun. 2009 (Year: 2009).*
Hai, "Introduction to the Species *Pouteria caimito* Radlk.—Abiu tree," The Worldwide Fruits website, May 5, 2016.
Prabhu et al., "Evaluation of antidiabetic activity of biologically synthesized silver nanoparticles using Pouteria sapota in streptozotocin-induced diabetic rats," Journal of Diabetes, 10, 28-42, Epub May 29, 2017.
Khatami et al., "Core@shell Nanoparticles: Greener Synthesis Using Natural Plant Products," Applied Sciences, Mar. 10, 2018, 8, 411.
Moore CJ, Montón H, O'Kennedy R, Williams DE, Nogués C, Crean C, Gubala V. Controlling colloidal stability of silica nanoparticles during bioconjugation reactions with proteins and improving their longer-term stability, handling and storage. J. Mater. Chem. B. 2015;3:2043-2055.
Cecilia VF, Joao Paulo SP, Inês Sabioni R, Sueli Maria G, Christopher WF, Carlos FSC, Luiz AS, Dâmaris S. Potential radical-scavenging activity of Pouteria caimito leaves extracts. J Appl. Pharm. Sci. 2016;6 (07):184-188.

\* cited by examiner

*Primary Examiner* — Michael P Cohen
(74) *Attorney, Agent, or Firm* — Richard C. Litman; Nath, Goldberg & Meyer

(57) ABSTRACT

The fruit-derived core-shell nanospheres uses mixing silver nitrate and *Pouteria caimito* extract as a method for the green synthesis of silver nanoparticles, followed by coating the nanoparticles with silica. These core-shell nanospheres may be produced by aqueous extraction of dried *P. caimito* fruit and mixing and incubating the resulting *P. caimito* extract with silver nitrate to produce a nanoparticle composition including the silver nanoparticles. The nanoparticles may be subsequently coated with silica by mixing with a silica precursor. The core-shell nanospheres show activity against oral cancer.

14 Claims, 9 Drawing Sheets

FRUIT-DERIVED CORE-SHELL NANOSPHERES

BACKGROUND

1. Field

The disclosure of the present patent application relates to nanotechnology, and particularly to fruit-derived core-shell nanospheres made using silver nitrate and *Pouteria caimito* to form silver nanoparticles coated with a silica shell:

2. Description of the Related Art

Nanoparticles have demonstrated important uses in a variety of fields. In particular, silver nanoparticles have been applied in electronics, biosensing, plasmonics, optics, and medicine. In particular, silver nanoparticles have demonstrable antibacterial properties. Core-shell nanoparticles provide potentially useful and largely unexplored benefits over single material nanoparticles. For example, a silica coating on metal nanoparticles may increase colloidal stability of the nanoparticles in solution, and control or limit the distance between core particles.

Synthesis of silver nanoparticles for use alone or in core-shell nanoparticles has been achieved by a variety of methods, including physicochemical, thermal decomposition, electrochemical, microwave-assisted, sonochemical, solvothermal, photosynthesis, photochemical reduction, chemical reduction, and continuous-flow methods. These methods are often costly or produce byproducts that pose increased risks to human health and the environment.

Thus, fruit-derived core-shell nanospheres solving the aforementioned problems are desired.

SUMMARY

The fruit-derived core-shell nanospheres are made using silver nitrate and *Pouteria caimito*, the method including providing a solution including silver nitrate; providing an extract of the *Pouteria caimito* plant or plant part(s); mixing the silver nitrate solution and the extract solution to form an aqueous mixture; and resting the aqueous mixture for a period of time to form biosynthesized silver nanoparticles (BAgNP; alternatively referred to as bio-silver nanoparticles). The BAgNP are mixed with a tetraethoxysilane solution, and then washed and dried for shell synthesis, resulting in silver-core,-silica-shell nanospheres, referred to hereinafter as BAg@$SiO_2$, or alternatively, core-shell nanospheres. The BAg@$SiO_2$ nanospheres have shown anticancer activity against oral cancer. The synthesis method is inexpensive and environmentally friendly.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
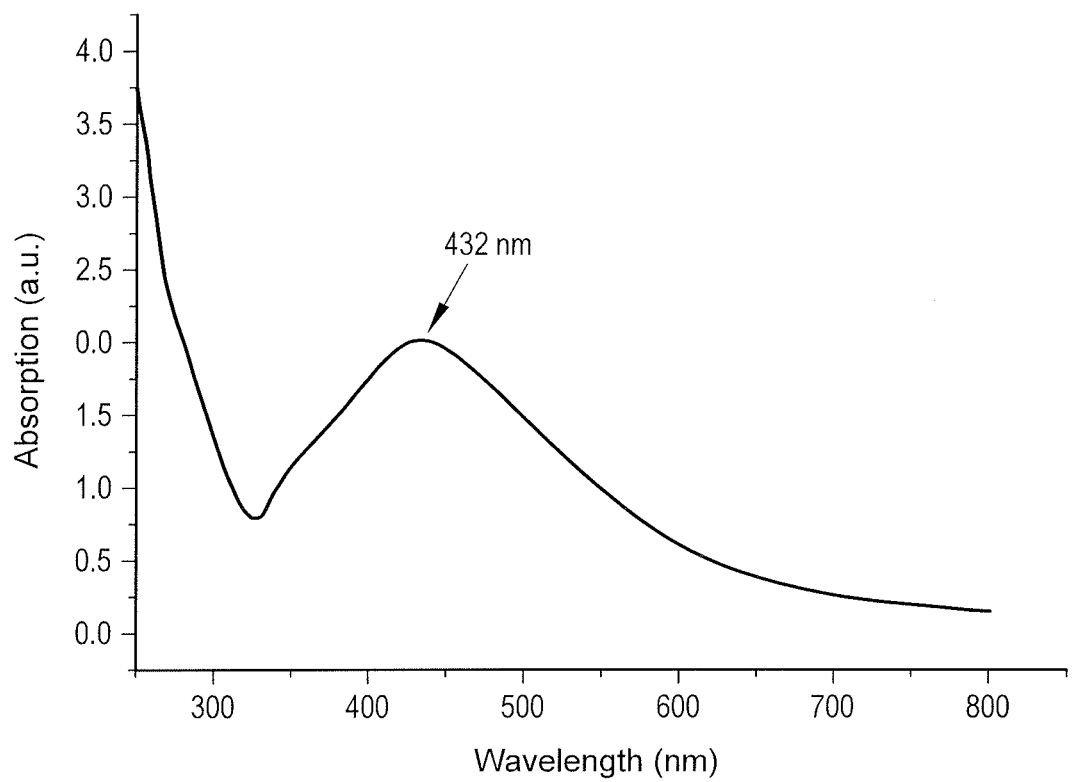
FIG. 1 is the UV-Visible spectrum of silver nanoparticles synthesized from silver nitrate and *Pouteria caimito* fruit.

The fruit-derived core-shell nanospheres includes a first step of mixing silver nitrate with a *Pouteria caimito* fruit extract to form bio-silver nanoparticles (BAgNP) and a second step of mixing the bio-silver nanoparticles with a silica precursor to form silica-coated silver nanoparticles (BAg@$SiO_2$). The silica-coated silver nanoparticles can be core-shell nanospheres in shape, with diameters ranging from 15 nm to 30 nm. In the exemplary synthesis discussed below, BAg@$SiO_2$ nanospheres were fabricated having sizes in the range of 16.85 nm to 25.42 nm (average size 18.19 nm). As used herein, the phrase "silver nanoparticles" is defined to include nanoparticles of pure silver metal, as wells as nanocomposites of pure silver metal coated or capped by elements or compounds extracted from *Pouteria caimito* or otherwise agglomerated into nanoparticles or incorporating *Pouteria caimito* extracts into the crystalline structure of the silver nanoparticles, as evidenced by EDX analysis.

The extract can be prepared by collecting one or more plant parts of the *P. caimito* plant for use as the extraction substrate. Suitable plant parts can include, for example, the leaves, flowers, stems, and/or roots of *P. caimito*. Prior to extraction, the *P. caimito* plant or plant part may be washed thoroughly one or more times with tap water and/or distilled water, e.g., triple distilled water. For example, in the exemplary synthesis discussed below, whole *P. caimito* plants were seeded and washed with running tap water, and then with distilled water. The washed *P. caimito* may then be dried, e.g., shade dried, at room temperature to provide dried *P. caimito*. The shade-drying may proceed for at least a day, and the washed *P. caimito* may be cut into sections to aid in drying. For example, in the exemplary synthesis discussed below, the shade-drying proceeded for three days, and the washed *P. caimito* were cut into sections around 0.2 to 0.4 inches. The dried *P. caimito* may then be powdered by grinding, blending, or any other conventional means. For example, in the exemplary synthesis discussed below, the dried *P. caimito* was powdered by using a blender at a speed of 15000 rpm for 3 mins. Powdered *P. caimito* may then be suspended in water, e.g., triple distilled water to produce the *P. caimito* extract. For example, in the exemplary synthesis discussed below, 5 grams of the powdered *P. caimito* was stirred well for 5 minutes and then suspended in about 500 mL of triple distilled water for about 24 hours. The *P. caimito* extract may be filtered using filter paper, a muslin cloth, or any other conventional means, producing filtered *P. caimito* extract. In the exemplary synthesis discussed below, a muslin cloth was used, resulting in exemplary *P. caimito* extract. The *P. caimito* extract may be used immediately after filtering.

The biogenic synthesis of the BAgNP may be achieved by mixing the *P. caimito* extract with silver nitrate ($AgNO_3$). For example, about 10 mL of the filtered *P. caimito* extract can be mixed with about 250 mL of 1 mM $AgNO_3$. In the exemplary synthesis discussed below, the $AgNO_3$ in *P. caimito* extract was mixed for 10 minutes and then allowed to incubate at room temperature for 48 hours. The mixture may be incubated at room temperature in a darkened location until a color change occurs from colorless to brown, indicating the formation of BAgNP. The mixture may then be centrifuged, e.g., at about 15,000 rpm for about 20 minutes. The supernatant may be discarded, and the pellet re-suspended in distilled water. The centrifugation and resuspension steps may then be repeated multiple times in order to remove impurities, for example, three times. The final resuspension may then be dried using conventional means, such as an oven, producing BAgNP or a nanoparticle composition including BAgNP and *P. caimito* extract components. For example, in the exemplary synthesis discussed below, the pellet was washed and centrifuged three times, and then dried in an oven at 40° C. for 12 hours. Once completely dry, the pellet may appear black. In the examples discussed below, the dried black colored material was collected in powder form and sampled for characterization of BAgNP by XRD, TEM, FTIR, and EDX with a SEM.

Silica coating of BAgNP may be executed using the following method. BAgNP may be mixed with a silica precursor. The dried BAgNP may first be suspended in water before mixing with the silica precursor. The silica precursor may be tetraethoxysilane (TEOS). For example, in the exemplary synthesis discussed below, all under continuous stirring, 500 mg of dried BAgNP was dissolved with 250 mL of distilled water and 4 mL of the aqueous BAgNP solution was mixed with 20 mL of ethanol, followed by 0.6 mL of ammonia (28%, Fluka) and then 0.5 mL TEOS (98%, Fluka). The mixture of BAgNP with silica precursor is mixed and incubated for sufficient time to form a silica coating on the BAgNP, resulting in $BAg@SiO_2$ in solution. For example, in the exemplary synthesis discussed below, the mixture was stirred continuously using a magnetic stirrer for 24 h at room temperature. The $BAg@SiO_2$ in solution may be isolated by any conventional means, for example, centrifugation or settling, and washed with water. Exemplary synthesized $BAg@SiO_2$ in solution was centrifuged at 5,000 rpm for 15 mins; the supernatant was discarded, and the pellet was dispersed in deionized water. This process was repeated three times for removal of ammonia, isopropanol and unreacted TEOS. After washing, the $BAg@SiO_2$ may be dried. For example, in the exemplary synthesis, the exemplary synthesized $BAg@SiO_2$ was kept in an oven at 40° C. for 12 hours to dry. The resulting powdered $BAg@SiO_2$ was used for analyses for physiochemical characterization and related coating confirmation studies, such as XRD, ATR-FTIR, TEM and EDX with a SEM.

A core-shell nanosphere composition including $BAg@SiO_2$ can be administered to a patient in need thereof. For example, a therapeutically effective amount of the composition can be administered to a patient suffering from cancer, in particular oral cancer. The therapeutically effective amount can be about 1-5 mg/kg.

The core-shell nanosphere composition can be admixed with a suitable pharmaceutical carrier, including, but not limited to water, glycols, oils, alcohols, flavoring agents, preservatives, coloring agents, starches, sugars, diluents, granulating agents, lubricants, binders, disintegrating agents, and the like. The composition can be administered by any conventional route of administration, including, but not limited to, intravenous, oral, subcutaneous, intramuscular, intradermal and parenteral. Depending on the route of administration, the composition can be constituted into any form. For example, forms suitable for oral administration include as pills, gel caps, tablets, caplets, capsules (each including immediate release, timed release and sustained release formulations), granules, powders, and syrups.

Example 1

Extraction of *P. caimito* Fruit

Fruit was collected from fresh *P. caimito* from Riyadh, Saudi Arabia. An aqueous extraction was prepared using seeded whole *P. caimito* fruit. The fruit were washed first with tap water and then with triple distilled water, and cut into small pieces (0.2-0.4 inches). The washed *P. caimito* fruit pieces were shade-dried for about three days. The shade-dried *P. caimito* fruit were then powdered using a blender at 15000 rpm for 3 mins. About 5 grams of powered *P. caimito* was suspended in 500 mL of triple distilled water for 24 hours, producing *P. caimito* extract. The *P. caimito* aqueous extract was filtered using a muslin cloth, producing filtered *P. caimito* extract.

Example 2

Biogenic Synthesis of BAgNP and $BAg@SiO_2$

A quantity of 10 mL of filtered *P. caimito* extract was mixed with about 250 mL of 1 mM $AgNO_3$ and kept at room temperature in the dark for 48 hours. The color of the reaction mixture changed from colorless to brown, indicating the formation of BAgNP. The mixture containing BAgNP was centrifuged at 15,000 rpm for 20 min, the supernatant was discarded, and the pellet was dispersed in distilled water. This process was repeated three times for removal of impurities, and the pellet was dried in an oven at 40° C. for 12 hours. The resulting dried BAgNP were used for further studies or suspended in water for synthesis of BAg@SiO$_2$.

Silica coating of BAgNP was achieved by mixing 4 mL BAgNP with 20 mL of ethanol, followed by 0.6 mL of ammonia (28%, Fluka) and 0.5 mL TEOS (98%, Fluka). The mixture was stirred continuously by using a magnetic stirrer for 24 h under constant room temperature, at which point the mixture contained synthesized BAg@SiO$_2$. The synthesized BAg@SiO$_2$ in solution was centrifuged at 5,000 rpm for 15 mins, the supernatant was discarded and the pellet was dispersed in deionized water. This process was repeated three times for removal of ammonia, isopropanol and unreacted TEOS impurities. After complete washing, the resulting pellet was kept in an oven at 40° C. for 12 hours to dry. The resulting BAg@SiO$_2$ powder was used for analyses for physiochemical characterization and related coating confirmation studies, such as XRD, ATR-FTIR, TEM, and EDX with a SEM.

Example 3

Characterization of BAgNP and BAg@SiO$_2$

Bio-reduction of Ag$^+$ ions to colloidal nanoparticles was visually observed by a color change from colorless (AgNO$_3$ solution) to brown (BAgNP).

UV-visible spectroscopic analysis of BAgNP was used to further confirm nanoparticle synthesis. The absorption of light by the nanoparticles at different wavelengths provides an indication of particle size, while breadth of the absorption peaks signifies the particle size distribution. FIG. 1 shows UV spectra of BAgNP fabricated as described above, wherein the AgNO$_3$ and *Pouteria caimito* fruit extract are allowed to react for 48 hours. The highest absorbance peak appears at 432 nm, which confirms formation of BAgNP.

Figure 2A:
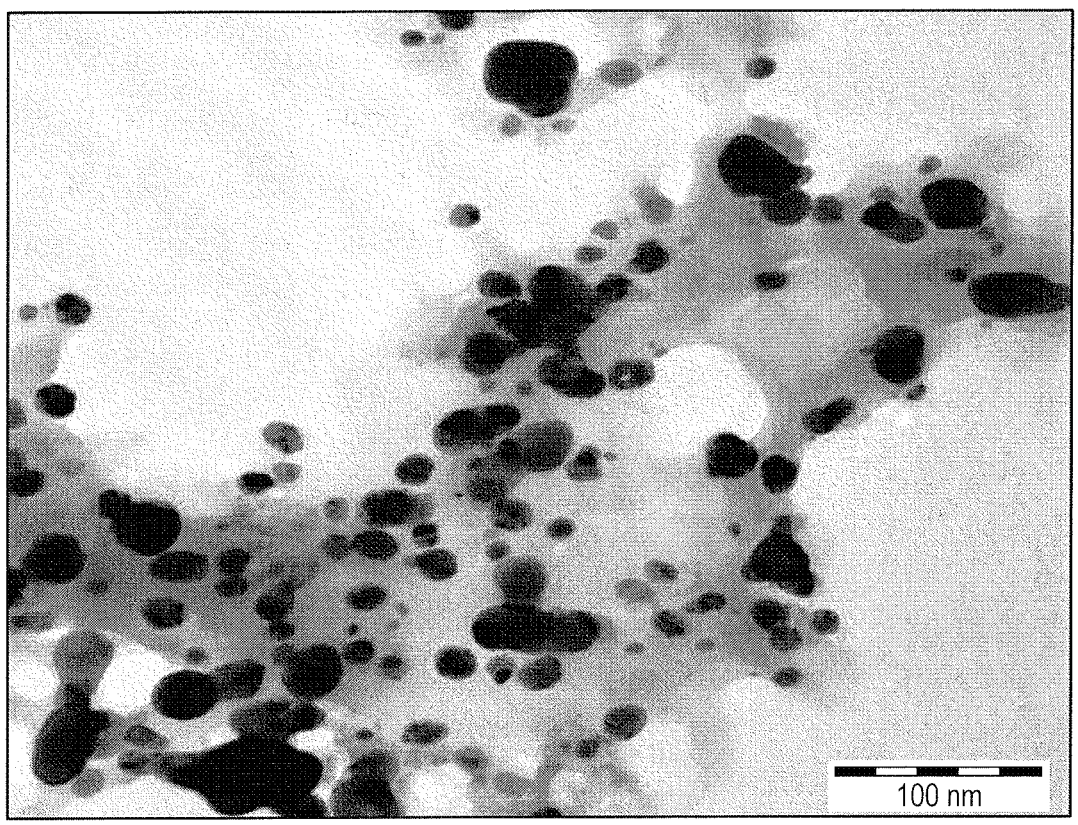
FIG. 2A is Transmission Electron Microscopy (TEM) micrograph of silver nanoparticles synthesized from silver nitrate and *Pouteria caimito* fruit.
Figure 2B:
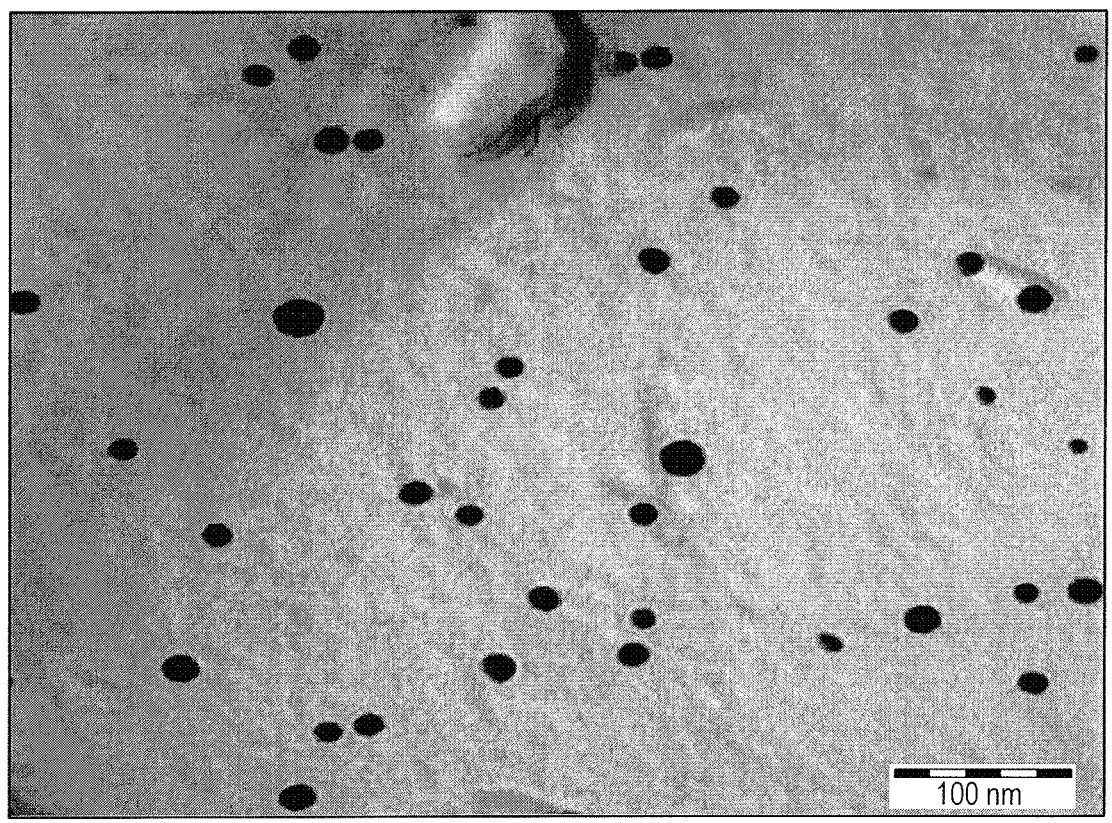
FIG. 2B is a TEM micrograph of core-shell nanospheres prepared from the nanoparticles of FIG. 2A.

Bio-silver nanoparticles and core-shell nanospheres were imaged by transmission electron microscopy (TEM), as shown in FIG. 2A and FIG. 2B, respectively. Bio-silver nanoparticles appeared spherical in shape with diameters in the range of 14.56 nm to 22.85 nm. Core-shell nanospheres appeared as core-shell nanosphere structures with outer diameters in the range of 16.85 nm to 25.42 nm.

Figure 3A:
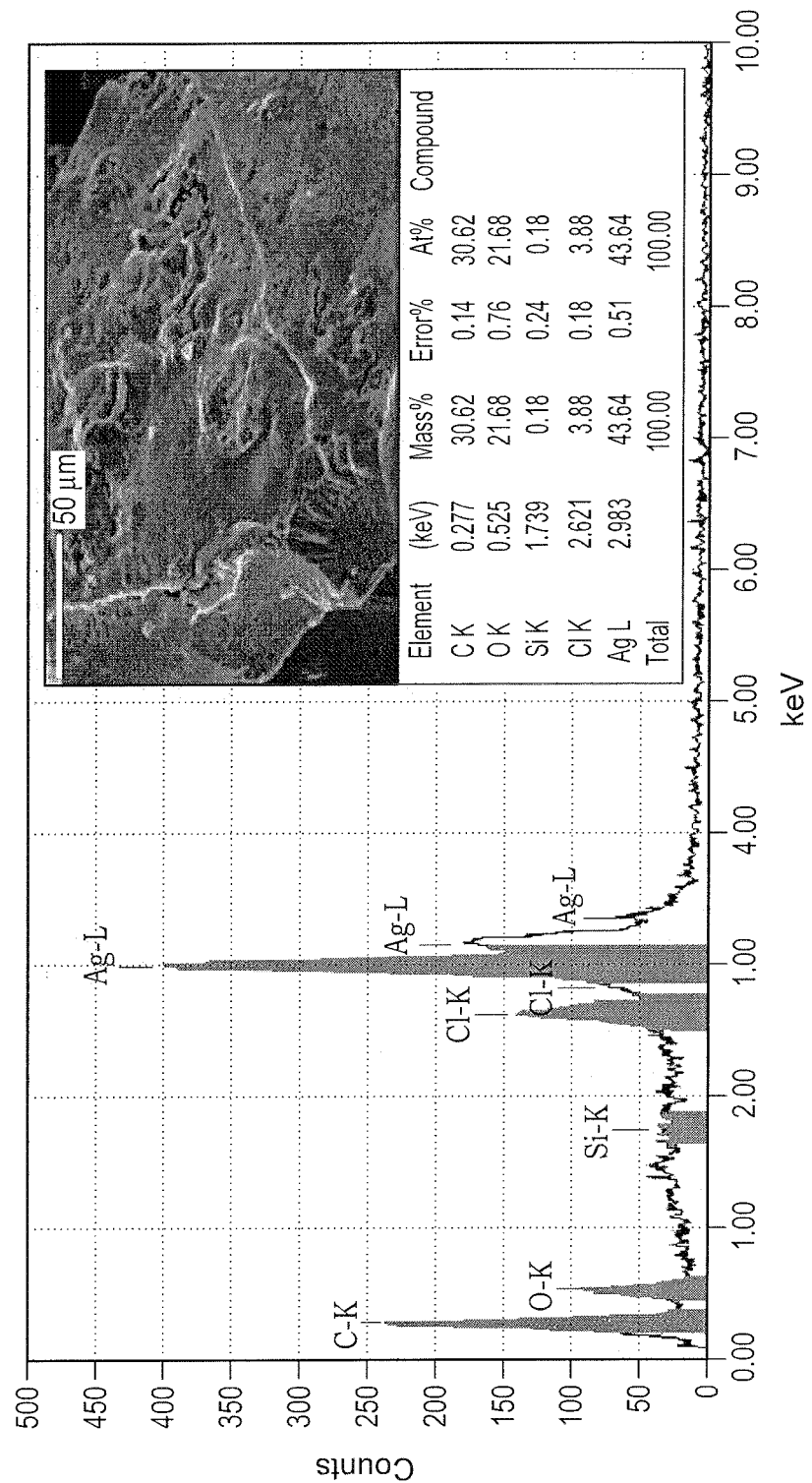
FIG. 3A is an Energy Dispersive X-Ray Diffraction (EDX) spectrum of silver nanoparticles synthesized from silver nitrate and *Pouteria caimito* fruit.
Figure 3B:
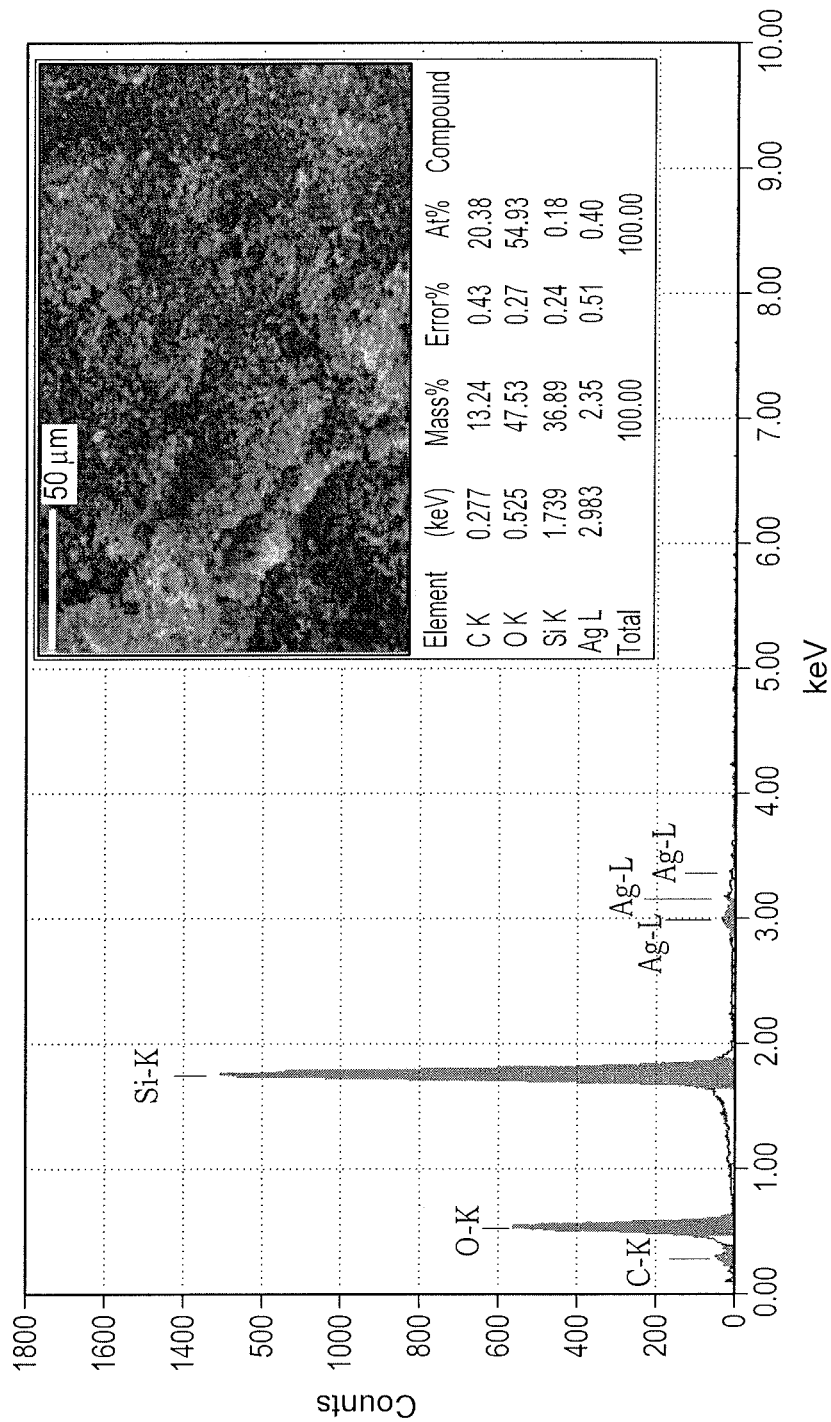
FIG. 3B is an EDX spectrum of core-shell nanospheres prepared from silver nanoparticles synthesized from silver nitrate and *Pouteria caimito* fruit.

Organic components of bio-silver nanoparticles before shell formation and formation of core-shell nanospheres were analyzed by Energy Dispersive X-Ray Diffraction (EDX) using SEM analysis, the results being shown in FIGS. 3A and 3B, respectively. The EDX peak of the bio-silver nanoparticles confirmed the presence of Ag as a major component, as well as others elements such as C, O and Cl, which indicates presence of these organic molecules, likely contributed by the *P. caimito* extract so that the silver nanoparticles are a silver nanocomposite. The EDX peak of core-shell nanospheres indicates that silicon is a significant surface component and also indicates Ag, suggesting formation of a silica coat around the bio-silver nanoparticles.

FTIR and ATR-FTIR spectroscopic analyses were performed on the exemplary bio-silver nanoparticles and core-shell nanospheres, respectively. These results are shown in FIG. 4A and FIG. 4B, respectively.

Figure 4A:
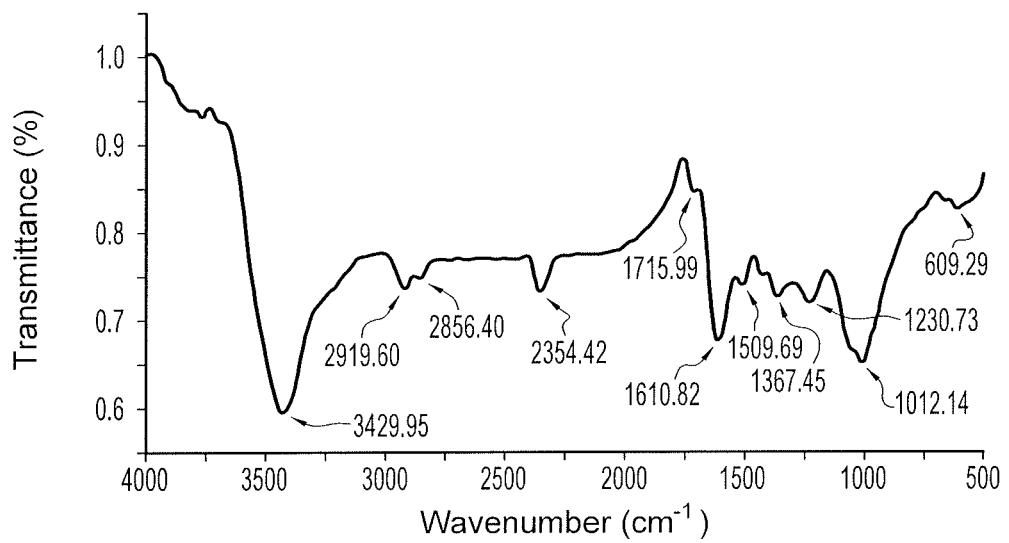
FIG. 4A is the Fourier Transform Infrared Spectroscopy (FTIR) spectrum of silver nanoparticles synthesized from silver nitrate and *Pouteria caimito* fruit.

The FTIR peaks evident in FIG. 4A indicate biomolecules from *Pouteria caimito* fruit extract are involved in the synthesis of the bio-silver nanoparticles. The absorption band at 3429 cm$^{-1}$ is likely due to N—H stretch of amino groups and possibly O—H stretch of a bound hydroxyl group. Absorption bands at 2919 and 2856 cm$^{-1}$ are indicative of C—H stretch in —CH$_3$ and —CH$_2$ functional groups. Absorption bands at 1715, 1610, and 1509 cm$^{-1}$ are attributed to protein amide groups or to C=O stretching vibrational groups. The absorption band at 1367 cm$^{-1}$ is attributed to O—H stretch. Absorption bands at 1012 and 1230 cm$^{-1}$ are likely due to the C—O groups. The absorption band at 609 cm$^{-1}$ is attributed to the presence of aromatics. The FTIR spectrum of the bio-silver nanoparticles in FIG. 4A supports amine (N—H), carboxyl (—C=O) and hydroxyl (—OH) groups of *Pouteria caimito* fruit extract are primarily involved in reducing Ag+ ions to Ag in the nanoparticles.

Figure 4B:
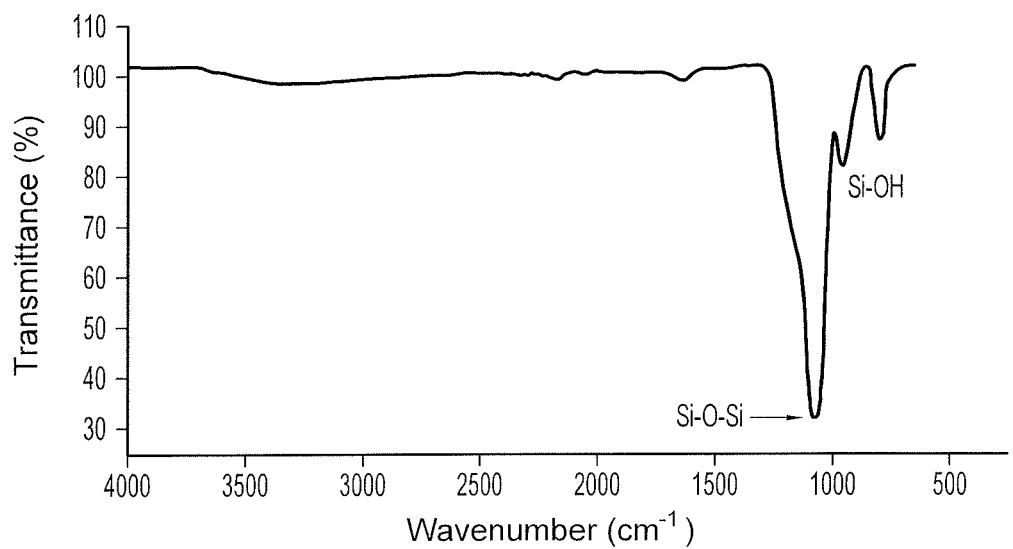
FIG. 4B is the Attenuated Total Reflectance Infrared (ATR-IR) spectrum of core-shell nanospheres prepared from silver nanoparticles synthesized from silver nitrate and *Pouteria caimito* fruit.

The ATR-FTIR peaks in FIG. 4B indicate primarily silicon forming an outer layer around the bio-silver nanoparticles in the core-shell nanospheres. The ATR-FTIR spectrum of the core-shell nanospheres does not include measurable (N—H), carboxyl (—C=O) and hydroxyl (—OH) bands, which indicates the silicon coated the outer layer of the biogenic synthesized silver nanoparticles. A 1071 cm$^{-1}$ band represents asymmetric and symmetric stretching of Si—O—Si bond vibration. 957 cm$^{-1}$ and 795 cm$^{-1}$ bands are due to Si—OH band vibration.

Figure 5A:
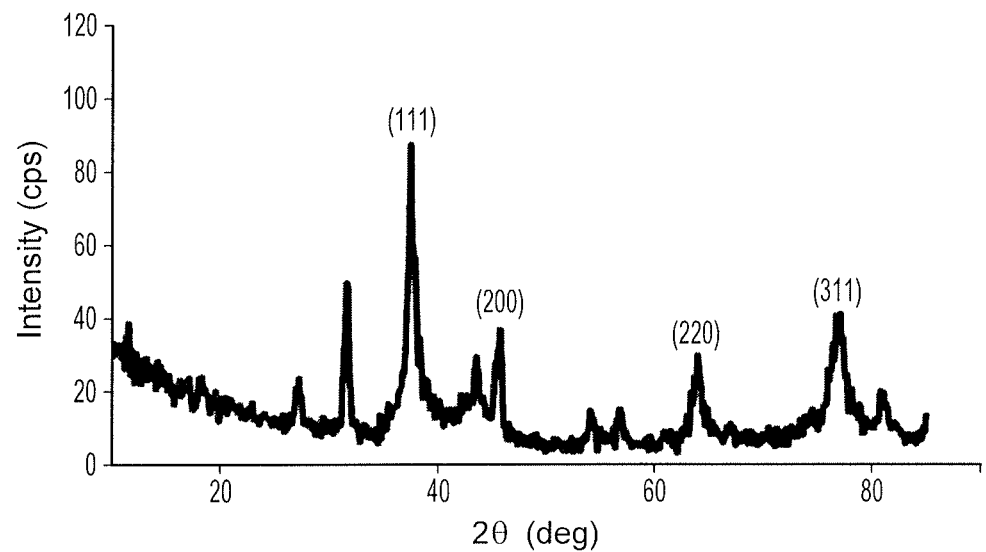
FIG. 5A is an X-Ray Diffraction (XRD) diffractogram of silver nanoparticles synthesized from silver nitrate and *Pouteria caimito* fruit.
Figure 5B:
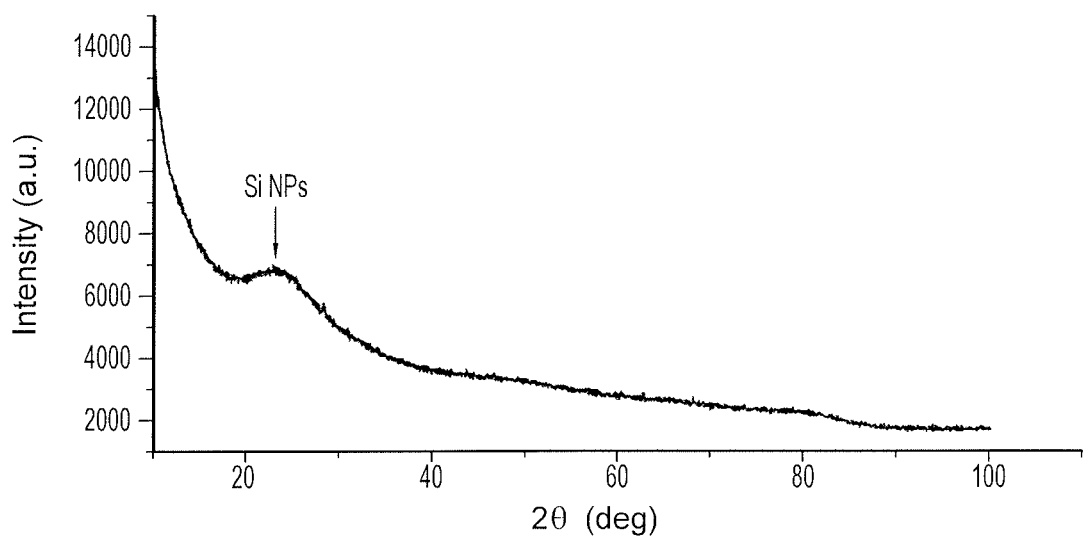
FIG. 5B is an X-Ray Diffraction (XRD) diffractogram of core-shell nanospheres prepared from silver nanoparticles synthesized from silver nitrate and *Pouteria caimito* fruit.

The XRD patterns of dry bio-silver nanoparticles and core-shell nanospheres are showed in FIG. 5A and FIG. 5B, respectively. The XRD pattern in FIG. 5A of bio-silver nanoparticles is consistent with a typical XRD pattern of face-centered cubic (fcc) silver, including signals indicating planes such as (111), (200), (220) and (311). Moreover, the residual peaks in the pattern in FIG. 5A are likely due to crystallization of biomolecules present in *Pouteria caimito* fruit extract. The XRD pattern in FIG. 5B of silica coated bio-silver nanoparticles evinces a broad peak at an angle of 20°-30°, which indicates the presence of a silica shell on the surface of the bio-silver nanoparticles.

The above-discussed data confirm the presently proposed method of producing core-shell nanospheres from silver nanoparticles reduced using *Pouteria caimito* fruit extract and subsequent silica coating. The present method produced bio-silver nanoparticles and core-shell nanospheres with consistently small size, high stability and no significant impurities.

Example 4

Core-Shell Nanosphere Anticancer Effect

The anticancer activity of the core-shell nanospheres, synthesized as disclosed herein, was evaluated against 7,12-Dimethylbenz(a)anthracene (DMBA)-caused buccal pouch carcinogenesis as described below.

7,12-Dimethylbenz(a)anthracene (DMBA)-caused buccal pouch carcinogenesis in hamster models is an ideal model for evaluating tumor-inhibiting activities of drugs from natural sources or nanomedicines. The core-shell nanospheres of the present disclosure were evaluated against DMBA-caused buccal pouch carcinogenesis in hamster models by evaluating the histopathological changes of buccal pouch and oral neoplasm incidence.

Forty hamsters were divided into 4 groups of 10 animals each. Group I animals received a normal pellet diet only and served as a control. In group II, the left buccal pouch of each animal was painted with 0.5% DMBA in liquid paraffin solution three times per week for 14 weeks. In group III, the left buccal pouch of each animal was painted with DMBA as in group II, and each animal received oral administration of BAg@SiO$_2$ (2 mg/kg body weight; in 0.5% DMSO) beginning 1 week before carcinogen exposure until the end of the experiments, continuing on days alternate to the DMBA painting. In group IV, each animal received oral administration of BAg@SiO$_2$ (4 mg/kg body weight; in 0.5% DMSO) throughout the experiments as a control to exclude toxic effects of the core-shell nanospheres. After the experimental period, all animals were sacrificed by cervical dislocation. Tumor volume and histopathological studies were conducted in buccal pouch tissues, which were excised and fixed with 10% formalin and embedded in paraffin. The embedded paraffin tissue samples were cut by rotary microtome into 2-3 µm sections and stained with hematoxylin and eosin.

Table 1 shows the tumor prevalence, tumor amount and tumor burden of normal control, BAg@SiO$_2$ treated, and untreated carcinogenesis animals. DMBA alone animals (Group 2) showed 100% tumor formation with mean tumor volume of 386.17 mm$^3$ and tumor burden of 1340.53 mm$^3$. The tumor incidence and volume were significantly decreased by administration of BAg@SiO$_2$ (orally at dose of 2 mg/kg).

Figure 6A:
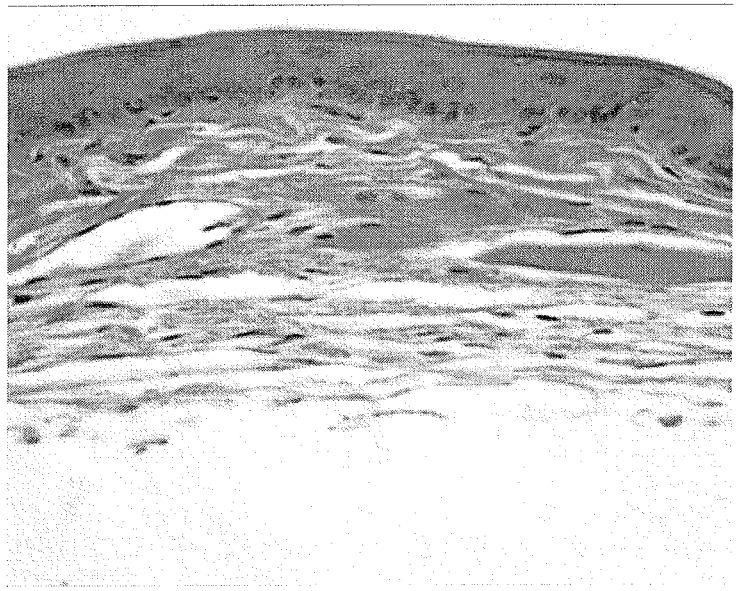
FIG. 6A is a photomicrograph of buccal tissue of a hamster from a control group not exposed to either core-shell nanospheres prepared from silver nanoparticles synthesized from silver nitrate and *Pouteria caimito* fruit or DBMA, showing normal epithelial tissue.
Figure 6B:
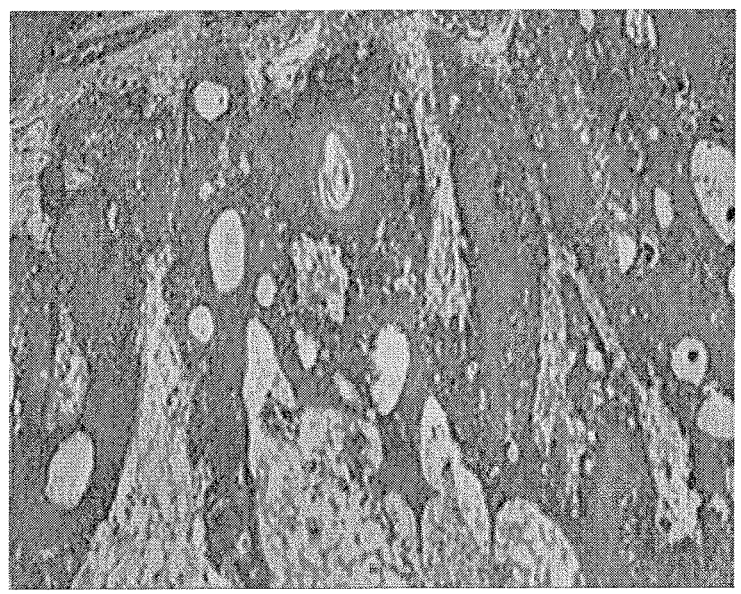
FIG. 6B is a photomicrograph of buccal tissue of a hamster showing squamous cell carcinoma of the epithelium induced by exposure to 7,12-dimethylbenz[a]anthracene (DBMA).
Figure 6C:
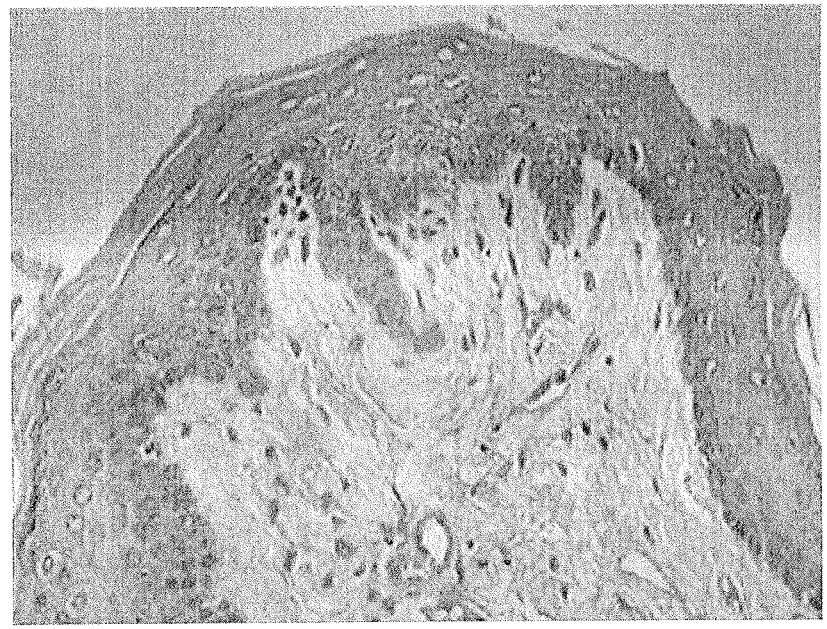
FIG. 6C is a photomicrograph of buccal tissue of a hamster exposed to 7,12-dimethylbenz[a]anthracene (DBMA) and also treated with core-shell nanospheres prepared from silver nanoparticles synthesized from silver nitrate and *Pouteria caimito* fruit, showing only a mild dysplasia.
Figure 6D:
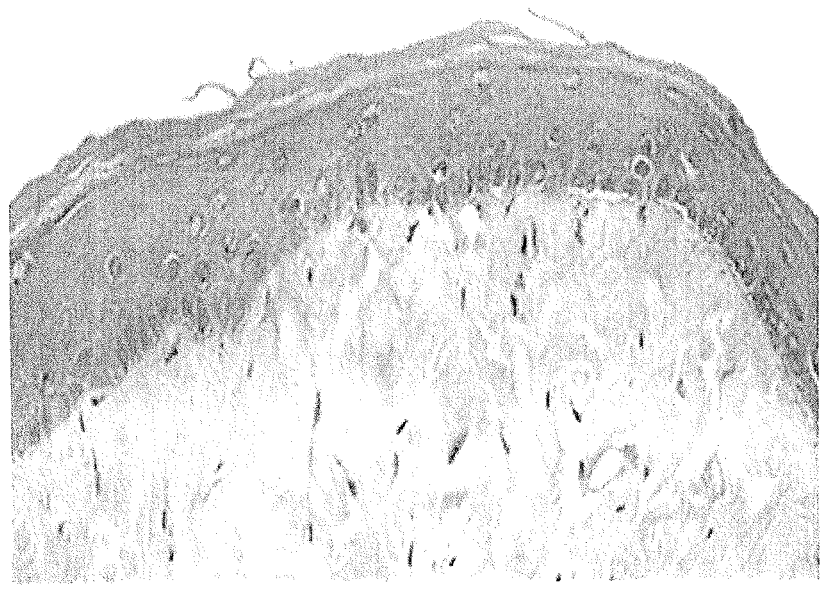
FIG. 6D is a photomicrograph of buccal tissue of a hamster from a control group treated with core-shell nanospheres prepared from silver nanoparticles synthesized from silver nitrate and *Pouteria caimito* fruit, but not exposed to DBMA, showing normal epithelial layers.

FIGS. 6A-6D show the buccal pouch histopathological appearance of normal, treated and carcinogenesis-alone animals. A well-differentiated squamous cell carcinoma of the epithelium, severe hyperkeratosis and hyperplasia were shown in DMBA-alone animal buccal pouches (FIG. 6B). Only a mild dysplasia was discerned in DMBA+BAg@SiO$_2$ treated animals (FIG. 6C). Normal animals treated with BAg@SiO$_2$ and normal control animals (not exposed either to DBMA or to fruit-derived core-shell nanospheres) each showed normal epithelial layers (FIG. 6D and FIG. 6A, respectively). The core-shell nanospheres, therefore, show preventive potential against DMBA-induced oral carcinogenesis.

Table 1 shows that the BAg@SiO$_2$ treatment prevented tumor formation. Tumor volume was calculated by used the following formula, $v=(4/3)\pi [D1/2][D2/2][D3/2]$ where D1, D2 and D3 are the three dimensional measurements (mm) of the tumor. Tumor burden was calculated by a multiplying tumor volume and the number of tumors/animal.

TABLE 1

Results of anti-cancer testing

| Parameter | Group I | Group II | Group III | Group IV |
|---|---|---|---|---|
| Tumor incidence (oral squamous cell carcinoma) | 0 | 100% | 0 | 0 |
| Total number of tumors/animals | 0 | 35/10 | 0 | 0 |
| Tumor volume (mm$^3$) | 0 | 386.17 ± 15.37 | 0 | 0 |
| Tumor burden (mm$^3$) | 0 | 1340.53 ± 71.27 | 0 | 0 |

It is to be understood that the fruit-derived core-shell nanospheres are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making fruit-derived core-shell nanospheres, comprising the steps of:
    mixing a *Pouteria caimito* extract with a silver nitrate solution to provide silver nanoparticles, and
    mixing the silver nanoparticles with a silica precursor to provide core-shell nanospheres, wherein the core comprises silver nanoparticles and the shell is silica.

2. The method of making fruit-derived core-shell nanospheres of claim 1, further comprising the step of extracting at least one plant part of *Pouteria caimito* to obtain the *Pouteria caimito* extract.

3. The method of making fruit-derived core-shell nanospheres of claim 2, wherein the *Pouteria caimito* plant parts include *Pouteria caimito* fruit.

4. The method of making fruit-derived core-shell nanospheres of claim 1, further comprising purifying the *Pouteria caimito* silver nanoparticles.

5. The method of making fruit-derived core-shell nanospheres of claim 1, wherein the core-shell nanospheres have a size ranging from about 10 nm to about 25 nm.

6. The method of making fruit-derived core-shell nanospheres of claim 1, wherein the silica precursor is tetraethoxysilane.

7. The method of making fruit-derived core-shell nanospheres of claim 1, wherein said step of mixing a *Pouteria caimito* extract with silver nitrate solution comprises mixing about 10 mL of the *Pouteria caimito* extract with about 250 mL of 1 mM silver nitrate.

8. The method of making fruit-derived core-shell nanospheres of claim 1, further comprising the step of incubating the mixture of *Pouteria caimito* extract and silver nitrate solution at room temperature for at least 24 hours to form the silver nanoparticles.

9. The method of making fruit-derived core-shell nanospheres of claim 1, further comprising, before mixing with the silica precursor, the step of purifying the silver nanoparticles by centrifugation and drying in an oven at about 40 degrees Celsius.

10. The method of making fruit-derived core-shell nanospheres of claim 9, further comprising, after drying the *Pouteria caimito* silver nanoparticles, the steps of rehydrating the *Pouteria caimito* silver nanoparticles in distilled water, and adding ethanol, ammonia and tetraethoxysilane.

11. A fruit-derived core-shell nanosphere composition, comprising:
    core-shell nanospheres having an average size ranging from about 10 nm to about 25 nm; and
    silver nanoparticles having *Pouteria caimito* extract components embedded therein, the silver nanoparticles forming the core of the core-shell nanoparticles, the shell being silica.

12. A method of treating oral cancer, comprising the step of administering to a patient in need thereof a therapeutically effective amount of the core-shell nanosphere composition of claim 11.

13. The method of treating oral cancer of claim 12, wherein the fruit-derived core-shell nanosphere composition is orally administered to the patient.

14. The method of treating oral cancer of claim 12, wherein the therapeutically effective amount of the core-shell nanosphere composition comprises between 1 mg/kg and 5 mg/kg.

\* \* \* \* \*